United States Patent [19]

Dattagupta et al.

[11] Patent Number: 4,724,202
[45] Date of Patent: Feb. 9, 1988

[54] USE OF NON-HYBRIDIZABLE NUCLEIC ACIDS FOR THE DETECTION OF NUCLEIC ACID HYBRIDIZATION

[75] Inventors: Nanibhushan Dattagupta, New Haven; Peter M. M. Rae; William J. Knowles, both of Hamden; Donald M. Crothers, Northford, all of Conn.

[73] Assignee: Molecular Diagnostics, Inc.

[21] Appl. No.: 560,462

[22] Filed: Dec. 12, 1983

[51] Int. Cl.$^4$ .................. C12Q 1/68; G01N 33/53; G01N 33/543
[52] U.S. Cl. .......................................... 435/6; 935/78; 436/811; 436/518; 435/7
[58] Field of Search ............... 436/508, 808, 501, 504; 435/6, 7; 935/76, 77, 78

[56] References Cited

U.S. PATENT DOCUMENTS

| | | | |
|---|---|---|---|
| 4,358,535 | 11/1982 | Falkow et al. | 435/6 |
| 4,395,486 | 7/1983 | Wilson et al. | 436/508 |
| 4,556,643 | 12/1985 | Paau et al. | 436/501 |
| 4,563,417 | 1/1986 | Albarella et al. | 435/6 |
| 4,582,789 | 4/1986 | Sheldon et al. | 435/6 |

FOREIGN PATENT DOCUMENTS

| | | |
|---|---|---|
| 4200 | 3/1984 | Australia . |
| 7500 | 10/1984 | Australia . |
| 40310 | 10/1985 | Australia . |
| 0079139 | 5/1983 | European Pat. Off. . |
| 0097373 | 1/1984 | European Pat. Off. . |
| 2125964 | 3/1984 | United Kingdom . |

OTHER PUBLICATIONS

Piette, et al., Proc. Natl. Acad. Sci., USA, vol. 80, pp. 5540-5544, Sep. (1983).
Weber, et al., The Operon, Reznikoff (ed.), Cold Spring Harbor Laboratory, 1980, pp. 155-175.
Salzman, et al., J. of Virology, Jun. 1979, vol. 30, No. 3, pp. 946-950.
Higuchi, et al., Proc. Natl. Acad. Sci., USA, vol. 73, No. 9, pp. 3146-3150, Sep. (1976).
Annual Review of Biophysics and Bioengineering, vol. 10, 1981, "The Interaction of Intercalating Drugs with Nucleic Acids", Helen M. Berman and Peter R. Young, pp. 87-114.
Accounts of Chemical Research, vol. 11, 1978, "Platinum Complexes: Probes of Polynucleotide Structure and Antitumor Drugs", Stephen J. Lippard, pp. 211-217.

Primary Examiner—Christine M. Nucker
Assistant Examiner—Stephen C. Wieder
Attorney, Agent, or Firm—Sprung Horn Kramer & Woods

[57] ABSTRACT

A detection probe comprising a hybridizable single stranded portion of nucleic acid connected with a non-hybridizable, single or double stranded nucleic acid portion, the non-hybridizable portion preferably including a recognition site for a particular protein.

51 Claims, 1 Drawing Figure

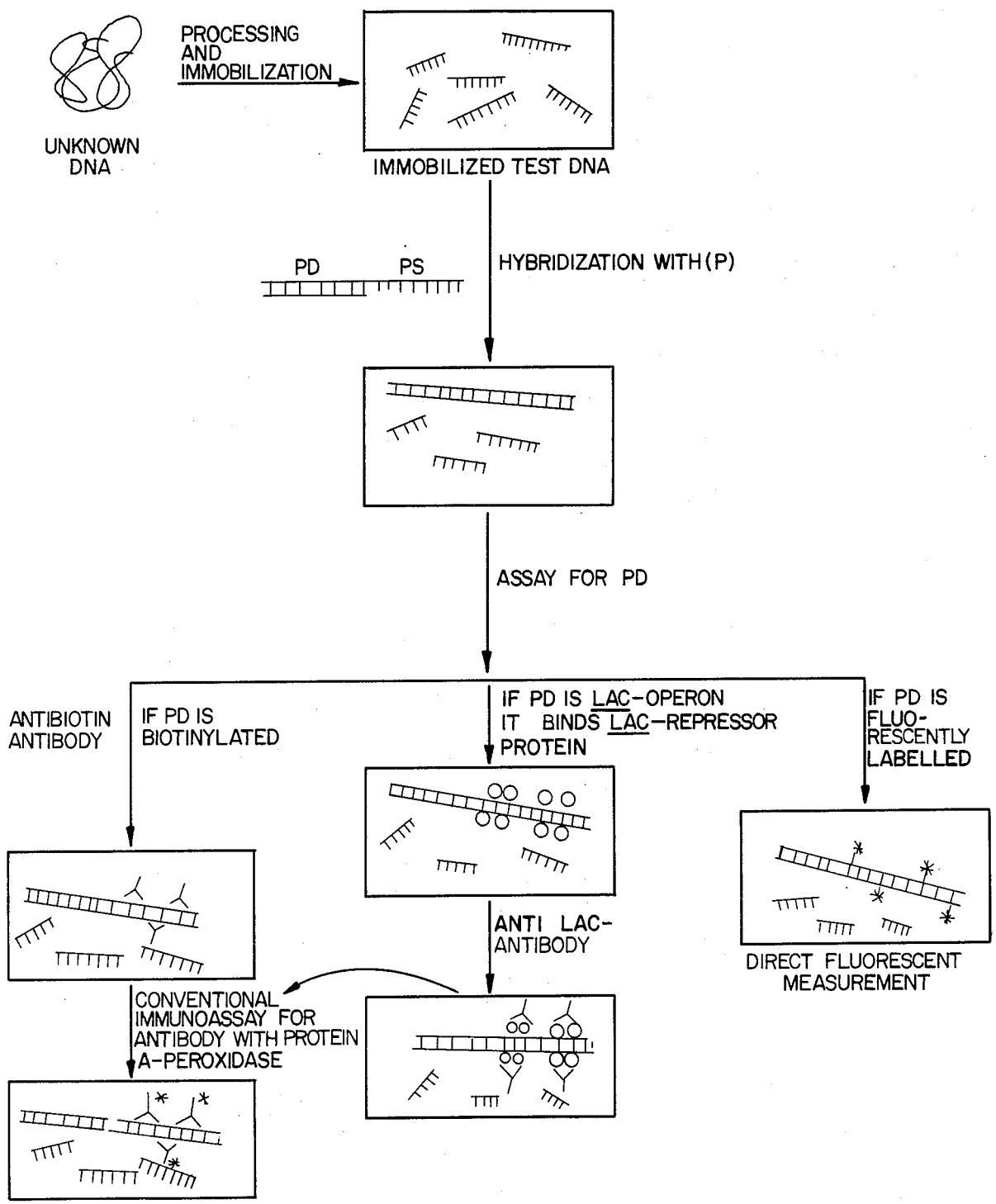

USE OF NON-HYBRIDIZABLE NUCLEIC ACIDS FOR THE DETECTION OF NUCLEIC ACID HYBRIDIZATION

This application relates to a labeled probe suitable for analytical and diagnostic purposes with regard to genetic constitution.

The evaluation of nucleic acid hybridizations is usually accomplished by detecting radioactivity introduced into a DNA:DNA or DNA:RNA hybrid via one member of a pair of complementary polynucleotides (the labelled member being designated the probe). Radiolabelling of the probe is effected by in vivo or in vitro polymerization of RNA or DNA under conditions in which precursors are isotopically tagged with $^3H$, $^{14}C$, $^{125}I$ or $^{32}P$, although it is also possible to label polynucleotides postsynthetically using $^{125}I$ or $^{32}P$-ATP. Each kind of radiolabelling has limitations, such as sensitivity of detection, isotope half-life, and hazard, and it is highly desirable that probe labelling be accomplished without resort to radioactivity.

Available alternatives are (i) attachment of haptens such as biotin to nucleic acid precursors, in which case an investigator is required to carry out in vitro polynucleotide syntheses in order to label a probe, then to detect the presence of biotinylated probe in a hybrid through the application of two or more steps; and (ii) the attachment of enzymes to oligonucleotide or polynucleotide probes, in which case hybrids are detected by their ability to convert a substrate to an optically or chemically distinguishable product. Both of these alternatives to radioactivity involve moderate to substantial changes in the chemical structure of probes, so that qualitative and/or quantitative effects on hybridization are a possibility, if not a reality.

Application Ser. No. 511,063, filed July 5, 1983, discloses a dual hybridization assay conducted with a known and an unknown nucleic acid sample and a nucleic acid-containing detection probe.

U.S. patent applicaion Ser. No. 511,063 describes a method for determining whether a nucleic acid in a test sample includes a particular nucleic acid sequence. Such method comprises the steps of:

(a) extracting the nucleic acids from a test sample, (b) digesting the extracted nucleic acids with a restriction enzyme thereby to effect restriction or not to effect restriction, depending on whether or not the restriction enzyme recognition site is precisely present in a sequence in the test DNA, (c) treating the product of (b) to form single-stranded nucleic acids, (d) contacting the single-stranded nucleic acids produced in (c) with first and second polynucleotide probes which are complementary to respective first and second portions of said sequence to be detected, the two portions being non-overlapping and immediately adjacent to the restriction site in question, and such contact being performed under conditions favorable to hybridization of said first and second probes to said sequence to be detected, hybridization with both of said probes to a test molecule being dependent upon whether in step (b) restriction did not occur, said first probe being incorporated with a distinguishable label, (e) separating, by means of said second probe, (i) any resulting dual hybridization product comprising said sequence to be detected hybridized to both said labeled first probe and said second probe, from (ii) any unhybridized and singly hybridized labeled first probe, and (f) by means of said label detecting any of said separated dual hybridization product which may be present.

U.S. patent application Ser. No. 511,063 also describes a suitable kit for running the test, which comprises (i) first and second probes each including nucleic acid sequences present in the nucleic acid of a test sample, the first probe carrying a distinguishable label and being soluble in a liquid in which the determination will be run, the second probe being fixed on a solid support, and (ii) a restriction enzyme which will cleave the test sample or fail to depending on the presence or absence of a particular nucleic acid sequence at the point separating sequences complementary to the first and second probes, whereby a positive determination test sample (no cleavage at the point) is capable of hybridizing with both the first and second probes so as thereby to affix the label to the solid support for subsequent reading. The presence of labeling material on the solid support is an index of the extent of dual hybridization.

The first and second probes are themselves formed in a special way. For example, a cloned beta-hemoglobin gene is digested by restriction enzymes which subdivide it into a number of fragments. In the case of detection of the sickle cell defect, the two of interest are a 340 bp (base pair) unit and a 201 bp unit. The fragments are separated from one another by subcloning, and one of them, the 340 bp unit fragment, is fixed to a solid support such as a nitrocellulose sheet or disc, constituting the fixed probe. The other fragment is labeled either with a radioactive group, or a chemically detectable group such as a modified base or a visually detectable group such as one which fluoresces or has characteristic absorbance of ultraviolet or infrared light.

A key to the procedure, in the difference between an affected and unaffected test sample, is that in one of them, upon treatment with a restriction enzyme, there will be fragments longer than each probe so as to be capable of hybridizing with both the fixed probe and the labeled probe whereas the other will not have such longer units, so it will be incapable of hybridizing with both. The dual hybridization is the key to attaching the label to the solid support via one test sample but not the other, such support being what is ultimately analyzed for the presence of label.

With sickle cell anemia as an example, a normal hemoglobin gene can be used to make probes of 340 and 201 bp, and sickle cell anemia hemoglobin DNA, upon digestion, will have a long fragment which covers the two and can dually hybridize, while similarly treated normal DNA will have no such fragment.

The manner of enzymatically digesting the DNA material for producing the probes and/or treating the test samples is known in the art, as are methods for the various separations.

Advantageously, the known sample, the separation probe, is immobilized on a solid support and contacted with the unknown and the instant labeled detection probe. The contact is performed under conditions favorable to hybridization. A portion of the unknown nucleic acid hybridizes with the immobilized probe. If the unknown also contains a nucleotide sequence which is complementary to the nucleotide sequence of the detection probe, a second or dual hybridization will then take place by which the detection probe becomes affixed to the solid support. If the unknown nucleic acid lacks the particular complementary nucleotide sequence, the detection probe will not hybridize therewith. Accordingly, the extent of the second hybridization, as indicated by the extent of labeling, is an indicator of the presence of the particular nucleotide sequence of interest in the unknown.

It then becomes necessary to determine how much of the second hybridization has taken place, i.e., how much of the detection probe is on the immobilized support.

The detection probe can be labeled with various labels which can be detected in systems that measure specific binding activity, fluorescence or enzyme activity. Such labels include radioisotopes, fluorescent radicals, enzymes and haptens. If too many labels are provided as in the case of fluorophores, they may interfere with the second hybridization. On the other hand, if there are too few labels, assay is less sensitive.

It is, accordingly, an object of the present invention to provide a detection probe (or the probe carrying the labels) which can be used in an assay without the disadvantages of radioactivity and without chemical modification of the probe components which could interfere with hybridization.

It is another object of the invention to provide a means of labeling a probe with a large number of readable labels resulting in relatively high sensitivity, without interfering with hybridization.

These and other objects and advantages are realized in accordance with the present invention pursuant to which there is provided a detection probe comprising a hybridizable single stranded portion of nucleic acid which can hybridize with the unknown, connected with a non-hybridizable single or double stranded nucleic acid portion, the non-hybridizable portion advantageously including a recognition or binding site for a particular protein. If the non-hybridizable portion is double stranded, one of the strands may be continuous, i.e., covalently associated, with the hybridizable portion.

The hybridizable portion of nucleic acid can be any of those described in greater detail with regard to the detection probe of Application Ser. No. 511,063, supra, as for example, a nucleotide sequence which is complementary to the genomic sequence responsible for sickle cell anemia.

The nucleic acid of the non-hybridizable portion can be a natural DNA sequence or synthetic oligonucleotide which contains a highly specific binding site or sites for a protein or proteins. The non-hybridizable portion can be specific for lactose (hereinafter referred to as lac) repressor protein which binds to an operator locus in the non-hybridizable portion, which operator must be double stranded, preferably after hybridization, as hybridization might sever the bond between operator and repressor. Accordingly, if the now-immobilized detection probe is contacted with a solution containing lac repressor protein, that protein will be selectively removed from the solution and will bind to the lac operator. Even if the concentration of nonspecific DNA in the hybridized sample is in 1000-fold excess, the binding to nonspecific sequences is negligible. In living cells, repressor proteins bind to their corresponding operator sequences to modulate transcription of a gene. When an operator sequence is covalently attached to other sequences, binding of repressor proteins is still specific for the operator.

In accordance with other aspects of the invention, there are provided several assay procedures utilizing the novel detection probes.

In one such assay for the presence of a particular nucleic acid nucleotide sequence in a sample, either the sample or a separation probe is immobilized on a support and, with a detection probe as described hereinabove, is subjected to hybridization, thereby affixing the non-hybridizable portion to the support. A protein is bound to the protein recognition site and thereby to the support. The protein is labeled at any stage, either before or after binding, and finally the label is assayed.

In another assay, after binding the protein and separating the support from the balance of the material, the support is treated in order to dissociate the protein from the hybridized detection probe and the dissociated protein is then assayed as by reading a label thereon, the label having been applied at any prior stage.

The invention is further described with reference to the accompanying drawing which is a schematic flow sheet of a hybridization and assay in accordance with the present invention.

Referring now more particularly to the drawing, the unknown DNA (to be tested) is processed as by digestion with a restriction enzyme, electrophoretic separation, southern transfer and/or simple denaturation. If not already immobilized, the DNA is then adsorbed on to a solid support (e.g., nitrocellulose paper) directly or by hybridization to a separation probe. The immobilized DNA is hybridized with a known probe. The known probe (P) has two regions. The region ps is single stranded and complementary to a specific gene to be detected and the region pd is a piece of double or single stranded, non-homologous DNA which carries the labels by which the labeling reaction will be detected. pd can be a specific sequence of double stranded DNA which binds a specific protein. For example, the double stranded DNA can be the lac promoter/operator sequence and then the protein is lac repressor. pd can also be a binding site for a specific antibody. pd can also be a specific single stranded, immunogenic polynucleotide sequence or poly $[d(G-C)]$ which, when treated with high salt, changes its structure and becomes immunogenic in the Z form. The pd portion can also be modified with psoralen derivatives or platinum-containing DNA binding ligands to produce immunogenic sites.

If pd is the lac promoter/operator sequence, pd will bind lac repressor protein after the hybridization. The protein can then be assayed by an antibody or by direct labeling. The double stranded pd portion can also be modified with hapten, e.g., biotin. Then the biotinylated hybrid can be detected in a known manner. The pd portion can also be modified with a number of fluorophores and can be assayed directly.

In a specific embodiment involving a lac operator-repressor system, the foregoing process involves at least the following four steps:

Step I: Grow bacteria and isolate lac repressor protein;

Step II: Covalently couple the detection probe to lac operator DNA and clone the adduct to have a large quantity of sample;

Step III: Prepare lac repressor—FITC or lac repressor-$\beta$-galactosidase adduct or anti-lac repressor antibody;

Step IV: Hybridization and detection of lac operator via label on the lac repressor.

Thereafter, the amount of bound lac repressor protein can be assayed in various ways. For example, antibodies thereto can be contacted with the bound lac repressor and protein A conjugated with an enzyme can be bound to the antibodies. The amount of bound enzyme can then be determined by the enzyme's catalytic reaction of its substrate in a conventional manner.

The amount of enzyme indicates the amount of lac repressor which, in turn, indicates the amount of hybridization which occurred earlier. Alternatively, the lac repressor protein can be fluorescently labeled or labeled with an enzyme and read in a conventional manner.

The double stranded region of the detection probe can also be specific for galactose repressor protein, lambda repressor protein, catabolite gene activator protein (CAP), Cro protein and the like. The foregoing description for assay of bound lac repressor protein applies equally to assay for the presence of these proteins. Such proteins can be purified from strains of *Escherichia coli*. The DNA sequences to which these proteins bind have been identified and isolated using recombinant DNA technology. The segment of *E. coli* DNA that contains the lac repressor binding site (the lac promoter-operator region) is transferred to recombinant plasmids that include segments of human DNA, such as portions of the gene encoding hemoglobin. These can be used without further genetic engineering to test for a number of hemoglobinopathies, such as some thalassemias and sickle-cell hemoglobinemia. Alternatively, in the dual hybridization scheme, two plasmids are used to determine if a sample of DNA from a human subject contains the genetic condition responsible for sickle cell hemoglobinemia. One plasmid is designated the separation probe. It contains DNA that is one flank of the dimorphic restriction enzyme cleavage site; it is immobilized as single stranded molecules on a solid support, and it is unlabeled. The second plasmid is designated the detection probe. It contains DNA that is the other flank of the dimorphic restriction site, and it has also been engineered to contain a segment of *E. coli* DNA that contains the lac promoter/operator region. Through the use of appropriate enzymes, the detector plasmid is made partially single stranded to the extent that β-globin gene sequences are available for hybridization while lac repressor recognition sites remain double stranded and available for protein binding.

Read out involving lac repressor protein provides highly specific recognition of the presence of the detection probe. It also opens a new set of possibilities for solution phase read out, because it is possible to release the repressor-antibody complexes from the operator DNA by addition of a β-galactoside, such as isopropylthio-galactoside. This allows automated batch or flow system processing.

In the foregoing description, the double stranded nucleic acid sequence contained a protein recognition site from the outset. However, if it did not contain such a site initially, it is possible to modify the DNA to create protein or antibody recognition sites for ease of reaction and detection.

Such modification can be effected by contact with reagents, such as furocoumarins, e.g., angelicins, psoralens, etc., as described more fully in Application Ser. No 513,932, filed July 14, 1983, now pending.

The most efficient and sensitive method of detection of nucleic acids such as DNA after hybridization requires radioactively labeled DNA. The use of autoradiography and enzymes makes the assay time consuming and requires experienced technical people. Recently, a non-radioactive method of labeling DNA has been described by Ward et al; they use the method of nick translation to introduce biotinylated U residue to DNA replacing T. The biotin residue is then assayed with antibiotin antibody or an avidin containing system. The detection in this case is quicker than autoradiography but the method of nick translation is a highly skilled art. Moreover, biotinylation using biotinylated UTP works only for thymine-containing polynucleotides. Use of other nucleotide triphosphates is very difficult because the chemical derivatization of A or G or C (containing $-NH_2$) with biotin requires elaborate techniques and highly skilled organic chemists.

U.S. patent application Ser. No. 513,932 describes labeling a nucleic acid by means of photochemistry, employing a photoreactive furocoumarin or phenanthridinium compound to link the nucleic acid to a label which can be "read" or assayed in a conventional manner. The end product is thus a labeled nucleic acid probe comprising (a) a nucleic acid component, (b) a furocoumarin or phenanthridinium compound photochemically linked to the nucleic acid component, and (c) a label chemically linked to (b).

The photochemical method described in Application Ser. No. 513,932 provides more favorable reaction conditions than the usual chemical coupling method for biochemically sensitive substances. By using proper wavelengths for irradiation, DNA, RNA and proteins can be modified without affecting the native structure of the polymers. By coupling the indicated photoactive agents to the substrate, the latter can be photochemically reacted to the desired system.

To produce specific and efficient photochemical products, it is desirable that the chemicals interact in the dark in a specific manner.

For coupling to DNA, aminomethyl psoralen, and aminomethyl angelicin and amino alkyl ethidium or methidium azides are the preferred compounds. They bind to double-stranded DNA and only the dark complex produces photoadduct. If the photoadduct of DNA has to undergo nucleic acid hybridization, the DNA should be denaturable. In that case, conditions are employed so that simultaneous interaction of two strands of DNA with a single photoadduct is prevented. It is also desirable that the number of modification sites is not more than one per hundred nucleotide bases. Angelicin derivatives are superior to psoralen compounds for monoadduct formation. If a single-stranded probe is covalently attached to some extra double-stranded DNA, use of phenanthridinium and psoralen compounds is desirable since these compounds interact specifically to double-stranded DNA in the dark.

The nucleic acid component can be singly or doubly stranded DNA or RNA or fragments thereof such as are produced by restriction enzymes or even relatively short oligomers.

The link (b) can be a furocoumarin such as angelicin (isopsoralen) or psoralen or derivatives thereof which photochemically will react with nucleic acids, e.g., 4'-aminomethyl-4,5'-dimethylangelicin and 4'-aminomethyltrioxsalen (4'-aminomethyl-4,5',8-trimethylpsoralen). It can also be a mono- or bis-azido aminoalkyl methidium or ethidium compound.

The label can be anything which can be assayed in known manner, e.g., a hapten such as biotin, an enzyme such as beta-galactosidase or horseradish peroxidase, papain, or a phycobiliprotein.

The individual reactions and reaction conditions are more-or-less well known. Advantageously, the link (b) is first combined with the label chemically and thereafter combined with the nucleic acid component. For example, since biotin carries a carboxyl group, it can be combined with the furocoumarin by way of amide or ester formation without interfering with the photochemical reactivity of the furocoumarin or the biological activity of the biotin. Other aminomethylangelicin, psoralen and phenanthridinium derivatives can be similarly reacted, as can phenanthridinium halides and derivatives thereof such as aminopropyl methidium chloride.

Alternatively, a bifunctional reagent such as dithiobis succinimidyl propionate or 1,4-butanediol diglycidyl ether can be used directly to couple the photochemically reactive molecule with the label where the reactants have alkyl amino residues, again in a known manner with regard to solvents, proportions and reaction conditions.

Certain bifunctional reagents such as glutaraldehyde are not suitable because, while they couple, they modify the nucleic acid and thus interfere with the assay.

The particular sequence in making the test material can be varied. Thus, for example, an amino-substituted psoralen can first be photometrically coupled with a nucleic acid, the product having pendant amino groups by which it can be coupled to the label. Alternatively, the psoralen can first be coupled to the enzyme and then to the nucleic acid.

If the label is an enzyme, for example, the product will ultimately be placed on a suitable medium and the extent of catalysis will be determined. Thus, if the enzyme is a phosphatase, the medium could contain nitrophenyl phosphate and one would monitor the amount of nitrophenol generated by observing the color. If the enzyme is beta-galactosidase, the medium can contain o-nitrophenyl-D-galacto-pyranoside which also will liberate nitrophenol.

The art is aware of other labels and how to test for their presence, e.g., for a biotin label use an avidin test, for histones use FITC, if there is free $-NH_2$ moiety one can directly post-label with FITC, etc.

Platinum-containing ligands can be similarly employed. The reagents render the non-hybridizable nucleic acid portion recognizable by protein. If the non-hybridizable portion is rendered immunogenic, such protein can be an antibody, i.e., an immunoglobulin, for example, a monoclonal antibody. The antibody can be bound to the non-hybridizable portion in an amount corresponding to the amount of furocoumarin creating the protein recognition sites. Antibody recognition sites can also be created when pd contains poly [d(G—C)] sequences, and the probe is exposed to high salt concentration.

Alternatively, the protein recognition site can be on a segment of the non-hybridizable portion other than nucleic acid per se. For example, the nucleic acid of the non-hybridizable portion can be linked by a member such as a furocoumarin to a chemical group such as biotin, the biotin constituting the protein recognition site.

The biotin can be assayed in a conventional manner, for example, with avidin or an anti-hapten antibody. The furocoumarin may be linked to a fluorophore, the fluorophore thereafter being assayed for fluorescence.

Labeling with the aforementioned proteins can be performed either before or after modification of the double stranded nucleic acid, preferably after.

Salts may also be used as a means of modifying the non-hybridizable portion to render it protein recognizable (e.g., poly [d(G—C)] or poly [d(G—$^{me}$C] changes to Z-form). Suitable salts include sodium chloride, other alkali and alkaline earth metal soluble salts of mineral acids, spermine or spermidines, advantageously in concentrations of at least about 1% by weight. Advantageously, the solvent is water. Both the salt-modified nucleic acid and the furocoumarin modified nucleic acid will be antigenic, e.g., will be capable of binding a specific antibody which can be assayed in conventional manner. For example, as hereinabove, the protein A can be conjugated with an enzyme which functions as the label in subsequent assay.

The invention also extends to assays involving detection probes wherein the non-hybridizable portion has been modified to attach a protein recognition site, as with a furocoumarin, as a link between the non-hybridizable double or single strand component and the protein recognition site, which can be a hapten or ligand. An immobilized separation probe or test sample is subjected to hybridizing conditions in the presence of a detection probe so modified to bind a protein and carrying a label, and the label is assayed. Alternatively, the protein may constitute an antibody and the antibody assayed immunologically in conventional manner, without formal labeling of the protein. As another alternative, if a hapten or ligand is at the protein recognition site, its presence can be assayed. The furocoumarin can also link a fluorophore and the fluorophore utilized as the assayable element.

The detection probes made and used as described above exhibit greater sensitivity than heretofore by virtue of the far greater number of labels per single stranded nucleic acid probe molecule than is possible with directly-labeling the probe molecules.

The invention will be further described with reference to the accompanying examples wherein all parts are by weight unless otherwise expressed.

EXAMPLE 1

Step I—Isolating lac Repressor Protein

*E. coli* strain BMH 461:

Δ (lac pro) ($\lambda C_1 857t68d$ lac $i^qz^+y^-$)/(F' lac $i^qz^+y^-$ pro+), developed by Muller-Hill et al., carries a thermally inducible lambda lysogen with a lac repressor gene and it overproduces the protein 1000-fold compared to the wild type strain. (Other *E. coli* strains can also be used to isolate the protein). The strain is grown substantially as described by Muller-Hill et al. and Platt et al. [Muller-Hill et al., *Proc. Natl. Acad. Sci.*, 59, 1259 (1968); Platt et al., in *Exp. in Mol Genetics* (ed., J. Miller) CSH, pp. 363–393 (1972)], as follows:

The cells are grown in a medium containing 3% Bactotryptone, 2% Bacto yeast extract (both from Difco) and 0.5% sodium chloride at 32° C. to an OD 550 of 3. Then the temperature is raised to 44° C. for 20 minutes to effect thermal induction. The cells are then incubated at 37° C. for 5 hours. The cells are collected from the culture by centrifugation at 6000 rpm and stored frozen at −80° C.

100 gms of cells are thawed and blended in a Waring blender and the supernatant after centrifugation is made up to 100 ml with a buffer comprising 0.2M Tris HCl, PH 6.9, 0.2M HCl, 10 mM mg acetate, 0.1 mM dithiothreitol, 5% (v/v) glycerol) and precipitated by adding 0.23 g/ml ammonium sulfate. The precipitate is collected by centrifugation at 10,000 rpm and redissolved in 5 ml of the foregoing buffer and desalted by exhaustive dialysis against a buffer solution comprising 0.12M potassium phosphate (PH7.4) 0.1 mM dithiothreitol, 5% (v/v) glycerol; 2% (v/v) dimethyl sulfate.

The lac repressor protein eluate is finally purified on a phosphocellulose column using phosphate buffer as above, with a linear gradient of 0.12 to 0.24 potassium phosphate.

The purity of the lac repressor-containing fraction is checked by SDS-polyacrylamide gel electrophoresis. The activity of the lac repressor protein is measured by its ability to bind operator-containing DNA in a known manner. The protein can be stored at −80° C. until use.

Step II—Covalently Coupling Detection Probe to lac Operator DNA

Preparation of a plasmid having both multiple copies of the lac repressor protein binding site (lac operator) and a portion of the $\beta$-hemoglobin gene, pursuant to *Molecular Cloning*, Maniatis et al., Cold Spring Harbor Laboratory, 1982.

Maniatis et al describe the following:

Cloning in Plasmids

In principle, cloning in plasmid vectors is very straightforward. The plasmid DNA is cleaved with a restriction endonuclease and joined in vitro to foreign DNA. The resulting recombinant plasmids are then used to transform bacteria. In practice, however, the plasmid vector must be carefully chosen to minimize the effort required to identify and characterize recombinants. The major difficulty is to distinguish between plasmids that contain sequences of foreign DNA and vector DNA molecules that have recircularized without insertion of foreign sequences. Recircularization of the plasmid can be limited to some extent by adjusting the concentrations of the foreign DNA and vector DNA during the ligation reaction. However, a number of procedures, described below, have been developed either to reduce recircularization of the plasmid still further or to distinguish recombinants from nonrecombinants by genetic techniques.

Insertional Inactivation

This method can be used with plasmids that carry two or more antibiotic-resistance markers.

The DNA to be inserted and the purified plasmid DNA are digested with a restriction enzyme that recognizes a unique site located in the plasmid within the tetracycline-resistance gene. After ligating the two DNAs at the appropriate concentrations, the ligation mixture is used to transform, for example, ampicillin-sensitive *E. coli* to ampicillin resistance. Some of the colonies that grow in the presence of ampicillin will contain recombinant plasmids; others will contain plasmid DNA that has recircularized during ligation without insertion of foreign DNA. To discriminate between the two kinds of transformants, a number of colonies are streaked in identical locations on plates containing ampicillin or tetracycline.

The colonies that survive and grow in the presence of tetracycline contain plasmids with an active tetracycline-resistance gene; such plasmids are unlikely to carry insertions of foreign DNA. The colonies that grow only in the presence of ampicillin contain plasmids with inactive tetracycline-resistance genes; these plasmids are likely to carry foreign DNA sequences.

In a few cases, methods have been developed to apply positive selection to obtain bacteria that are sensitive to an antibiotic from populations that are predominantly resistant. In this way, it is possible to select from recombinant plasmids that carry an inactivated antibiotic-resistance gene as a consequence of insertion of a foreign DNA sequence. The most useful of these systems is that described by Bochner et al (1980) and Maloy and Nunn (1981), who developed media containing the lipophilic, chelating agents fusaric acid or quinaldic acid, which allow the direct positive selection of Tet$^s$ clones from a population of Tet$^s$ and Tet$^r$ bacteria. For most strains of *E. coli*, approximately 90% of the colonies obtained on media containing tetracycline and fusaric acid were found to be Tet$^s$ when plated onto media containing tetracycline alone. It is, therefore, possible to select from a population of plasmids with insertions at the BamHI and SalI sites.

A similar technique has been developed to select for bacteria sensitive to paromomycin (Slutsky et al, 1980). This should allow the selection of derivatives of pMK16 that contain insertions at the SmaI or XhoI site (Kahn et al, 1979).

Although insertion of foreign DNA sequences within an antibiotic-resistance gene almost always leads to inactivation of that gene, at least one case is known where an insertion left the gene in a functional state. Villa-Komaroff et al (1978) found that insertion of a segment of rat preproinsulin cDNA into the PstI site of pBR322 does not inactivate the ampicillin-resistance gene. Presumably, a small piece of foreign DNA had been inserted that did not alter the reading-frame of the ampicillin-resistance gene, so that a fusion protein was formed which retained beta-lactamase activity.

Directional Cloning

Most plasmid vectors carry two or more unique restriction enzyme recognition sites. For example, the plasmid pBR322 contains single HindIII and BamHI sites.

After cleavage by both enzymes, the larger fragment of plasmid DNA can be purified by gel electrophoresis and ligated to a segment of foreign DNA containing cohesive ends compatible with those generated by BamHI and HindIII. The resulting circular recombinant is then used to transform *E. coli* to ampillicin resistance. Because of the lack of complementarity between the HindIII and BamHI protruding ends, the larger vector fragment cannot circularize efficiently; it, therefore, transforms *E. coli* very poorly. Therefore, most of the colonies resistant to ampicillin contain plasmids that carry foreign DNA segments forming a bridge between the HindIII and BamHI sites. Of course, different combinations of enzymes can be used, depending on the locations of restriction sites within vector and the segment of foreign DNA.

Phosphatase Treatment of Linear, Plasmid Vector DNA

During ligation, DNA ligase will catalyze the formation of a phosphodiester bond between adjacent nucleotides only if one nucleotide contains a 5'-phosphate group and the other a 3'-hydroxyl group. Recircularization of plasmid DNA can, therefore, be minimized by removing the 5' phosphates from both ends of the linear DNA with bacterial alkaline phosphatase or calf intestinal phosphatase (Seeburg et al, 1977; Ullrich et al, 1977). As a result, neither strand of the duplex can form a phosphodiester bond. However, a foreign DNA segment with 5'-terminal phosphates can be ligated efficiently to the dephosphorylated plasmid DNA to give an open circular molecule containing two nicks.

Because circular DNA (even nicked circular DNA) transforms much more efficiently than linear plasmid DNA, most of the transformants will contain recombinant plasmids.

Problems in Cloning Large DNA Fragments in Plasmids

Finally, the size of the foreign DNA to be inserted can also affect the ratio of transformants containing recombinant plasmids to those containing recircularized vectors. In general, the larger the insertion of foreign DNA, the lower the efficiency of transformation. Thus, when cloning large DNA fragments (less than 10 kb), it is especially important to take all possible measures to keep the number of recircularized vector molecules to a minimum. Even so, the background is relatively high, and it is usually necessary to use an in situ hybridization procedure (Grunstein and Hogness 1975; Hanahan and Meselson 1980) to identify recombinant transformants.

1. pHW104 is a derivative of pBR322 that has 4-5 copies of the 203 bp Hae III segment of the lac operon that contains the lac repressor binding site. The segment is tailed with Eco RI linkers, and tandem copies are inserted into the $Ap^R Tc^S$ vector pHW1 (a derivative of pBR322 prepared by Hae II digestion to lack the sequence 236 to 2352) at the Eco RI site.

2. pSS737 is a derivative of pBR322 that has the 737 bp Alu I segment of the human $\beta$-globin gene that contains about 0.5 kb of the gene and about 0.25 kb of upstream flanking sequence. The segment is tailed with Eco RI linkers and inserted into the Eco RI site of pBR322.

The procedure for putting the lac repressor binding sites and the segment of the $\beta$-globin gene in the single plasmid as in 1 and 2 above, is as follows:

a. Linearize pHW104 with Hind III; treat with alkaline phosphatase to prevent recircularization in step c.

b. Digest pSS737 with Hind III plus Fnu DII; collect the greater than 0.76 kb segment from a preparative agarose gel.

c. Ligate the products of steps a and b, then fill in free Hind III ends using the Klenow fragment of DNA polymerase and deoxyribonucleotide triphosphates.

d. Blunt-end ligate (c) molecules to make circular plasmids, then transform E. coli cells to ampicillin resistance.

e. Collect a number of $Ap^R$ colonies and grow cells for the minilysate production of small amounts of plasmid.

f. Check the plasmids for composition by restriction enzyme digestion. The desired plasmid has:
  i. a single Hind III site;
  ii. Eco RI segments of 2.2, 0.74 and 0.21 kb;
  iii. digestibility by Mst II;
  iv. Desirably a Cla I segment of about 0.75 kb, depending on the orientation of the globin gene insert.

The separation and detection probe for dual hybridization analysis of sickle cell defect are disclosed in detail in application Ser. No. 511,063, filed July 5, 1983, described hereinabove.

3. Use of a plasmid having both multiple copies of the lac repressor binding site and a portion of the $\beta$-hemoglobin gene as a hybridization probe:

For the plasmid to be a useful probe for the detection of $\beta$-globin gene sequences in a sample of DNA, the globin gene portion of the plasmid must be single stranded so that in a subsequent test it can hybridize to a sample of denatured DNA, and the lac operator region must be double stranded to allow binding of the lac repressor protein.

To achieve this, the plasmid product of (2) is linearized using Hind III, then is subjected to a controlled digestion by exonuclease III ($\lambda$ exonuclease or T4DNA polymerase can be similarly employed). Such treatment makes most or all of the globin gene portion single stranded, leaving most of the rest of the plasmid, including the copies of the lac operator region double stranded.

Alternatively, pairs of pEMBL plasmids (available from the European Molecular Biology Laboratories, Heidelberg) can be used. These plasmids contain a portion of the $F_1$ phage genome, so that they behave like phage M13 in producing single stranded DNA molecules. Unlike with M13, however, it is possible with pEMBL to collect both complementary strands of a plasmid in pure form simply by having the $F_1$ portion of the pEMBL genome in different orientation in two strains; it is the orientation of the $F_1$ genes in the plasmid that determines which of the two strands of the plasmid DNA will be secreted from infected bacteria as single stranded DNA phage.

For example, one plasmid, pEMBL8(+), is engineered to contain tandem copies of the lac repressor binding site plus a portion of the $\beta$-hemoglobin gene; another plasmid, pEMBL8(−), contains just the tandem copies of the lac repressor binding site. The single stranded DNA of pEMBL8(+) is hybridized to a sample of unknown DNA, and contact is made through sequence homology between the globin gene portion of the probe and complementary sequences in the sample. The lac operator portion of the probe is made double stranded for lac repressor binding by the annealing of pEMBL8(−) to the pEMBL8(+)-sample DNA complex.

It is possible to carry out such reactions with the replicative (but not the single stranded phage) form of M13 as well as with any plasmid DNA, but one has either to separate the complementary strands, or take considerable loss in hybridization efficiency by having both strands of a plasmid present in a hybridization mixture, where they can undesirably self-anneal.

Step III—(a) Labeling of the Protein with Fluorescein

Fluoresceinisothiocyanate (FITC) is dissolved in ethanol (5 mg solid/ml). To 2 ml of a 5 mg/ml protein solution from (I), 0.5 ml carbonate buffer (1M NaHCO$_3$—Na$_2$CO$_3$ buffer pH 9) is added, followed by 50 $\mu$l FITC solution. The mixture is shaken well and the free FITC is chromatographically separated from the bound molecules on a Sephadex G50 column using a buffer comprising 10 mM Tris, 1 mM EDTA, 50 mM KCl, pH 7.4. The labeled protein is collected in the void volume.

(b) Labeling with $\beta$-galactosidase Enzyme

Lac repressor protein from I and $\beta$-galactosidase (1:1 molar ratio) (alkaline phosphatase, horseradish peroxidase react similarly) are mixed in phosphate buffer and glutaraldehyde is added to final concentration of 0.2%. Reaction is allowed to proceed for 4 hours. The protein mixture is dialyzed against the same Tris EDTA buffer as in (a).

Step IV—Hybridization and Detection Via Labels on the Lac Repressor

Hybridization is done by fixing the separation probe to a solid support according to the example of application Ser. No. 511,063, supra, using as the detection probe that probe produced in II which carries the non-homologous DNA which is the lac repressor protein binding site. After hybridization, the solid support is washed with BSA solution 1% ω/v in Tris-EDTA buffer as in Example 1, Step III(a), and then lac repressor, labeled as in III(a), (b) or (c), is added. The bound repressor is assayed optically (in the example of fluorescein labeled repressor) or enzymatically (in the example of enzyme labeled repressor).

In patent application Ser. No. 511,063, immobilizing a separation probe and labeling a detector probe are described as follows: Plasmid containing the separation probe, e.g., a subclone of the 0.34 kb Hinf segment of pSS737, is treated with 0.1 m NaOH for 5 minutes, then chilled in ice. The sample is neutralized with an equal volume of 0.1N HCl, 0.9M NaCl, 0.09M Na citrate, then filtered under mild aspiration through a nitrocellulose filter (e.g., BA 85 from Schleicher and Schuell) that had been presoaked in 0.9M NaCl, 0.09M Na citrate (6×SSC; 1×Standard Saline Citrate is 0.15M NaCl, 0.015M Na citrate). The filter is then washed with 6×SSC, then 70% ethanol, and baked under vacuum at 80° C. for a few hours, or with no vacuum at 65° C. overnight. At this point, the filter is ready for hybridization procedures, but it can be stored dry for many months.

The purpose of the alkali treatment of plasmid is to denature the DNA. This renders it both capable of binding to nitrocellulose (native DNA does not) and available for subsequent hybridization with other single-stranded DNA. Neutralization of the denatured DNA solution with acid and the addition of salt (as 6×SSC) facilitate the binding of denatured DNA to nitrocellulose, and the low temperature inhibits reannealing of the plasmid while it is being loaded onto the nitrocellulose. Baking of the filter finally immobilizes the DNA.

Labeling of the detector probe with, for example, $^{32}P$ can be accomplished in several ways, all of which are standard methods: The ends of a plasmid that has been made linear by the action of a restriction endonuclease can be labeled either by a reaction in which polynucleotide kinase adds the terminal phosphate of gamma$^{32}P$—ATP to the 5′ end of DNA molecules; by the filing in of recessed 3′ ends that are generated by some restriction enzymes, through the use of the large (Klenow) fragment of E. coli DNA polymerase and alpha$^{32}p$-labeled deoxyribonucleoside triphosphates; or by the 3′ terminal addition of labeled nucleotides through the action of terminal deoxynucleotidyl transferase. More extensive labeling of a probe can be accomplished using phage T4 DNA polymerase, or by strand replacement DNA synthesis ("nick translation") using E. coli DNA polymerase, labeled triphosphates, and plasmid that has been randomly nicked by deoxyribonuclease I to produce numerous synthesis primer sites. Other labeling schemes that do not involve readioactivity are also possible.

EXAMPLE 2

Hybridized probe of Example 1 carrying the lac repressor protein can be assayed immunochemically as follows:

(a) Purified lac repressor protein from Example 1 is mixed 1:1 with Freund's complete adjuvant and injected into mice (25 μg protein into both hind foot pads) or rabbits (500 μg subcutaneously). One month later the polyclonal antibody response is titered and the antiserum from animals with strong responses is collected and used for the immunoassays.

(b) To the hybrid complex containing the lac repressor protein of Example 1, specific dilutions of the antiserum of (a) are incubated for 1 hour at room temperature. Unbound antibodies are washed 3 times with a buffer solution comprising 5 mM $NaH_2PO_4$, 150 mM NaCl (pH 7.4) and 0.04% Triton X-100. Protein A covalently coupled to horseradish peroxidase (Sigma Chemical Co. p 8651) diluted 1:8000 in PBS as above, is incubated with the hybridization complex of Example 1 for 30 minutes at room temperature and washed 3 times with the aforementioned buffer. The substrate o-phenylenediamine in citrate buffer containing $H_2O_2$, pH 5.6, is added and the enzymatic reaction product is measured at 492 nm. The amount of bound repressor is determined by comparison to standard quantitation curves.

EXAMPLE 3

The double stranded portion of the detection probe of Example 1 can be modified to bind a specific antibody as follows:

The detection probe is dissolved in 10 mM Tris 1 mM EDTA buffer and mixed with biotin-psoralen adduct as described in Example 1 of application Ser. No. 513,932, supra. The mixture is irradiated with 360 nm light at room temperature for 40 minutes. After the reaction, the sample is dialyzed against the hybridization buffer of Example 1, to exclude unreacted biotin-psoralen adduct.

The biotin-containing detection probe is then hybridized as in Step IV and the hybrid is assayed for the presence of biotin in known manner employing FITC-labeled avidin.

Example 1 of application Ser. No. 513,932 describes that 50 mg of N-hydroxysuccinimido biotin is dissolved in 2 ml dimethylsulfoxide (soln A). 10 mg of 4′ aminomethyl trioxsalen (structure 1) (or other aminoalxyl compounds) is dissolved in 10 ml (soln B) aqueous buffer solution pH approximately 8. Solutions (A) and (B) are mixed in a volume ratio of 1:10 and weight ratio of 10:1, so that the activated hapten is present in large excess. The reaction is allowed to proceed at 35° C. for 1 hour. The extent of the reaction is monitored by thin layer chromatography—on silica gel plates with a fluorescence indicators in a solvent 1½—methanol/acetic acid/chloroform. Under these TLC conditions unreacted aminomethyl trioxalane moves with the solvent front, whereas the product has a slower mobility. Biotin does not show any fluorescene but the adduct fluoreces because of trioxsalen. Growth of the new fluorescent spot and disappearance of the original fluorescent spot indicates the extent of product formation. Since the activated biotin is in large excess, fluorescence corresponding to the starting material vanishes on TLC after the completion of reaction. Excess active biotin is reacted with glycyl-glycine or lysine.

It is understood that the specification and examples are illustrative, but not limiting to the present invention and that other embodiments within the spirit and scope of the invention will suggest themselves to those skilled in the art.

What is claimed is:

1. A detection probe comprising a hybridizable single stranded portion of nucleic acid connected to a non-hybridizable, single stranded nucleic acid portion, the non-hybridizable portion including a recognition site for a particular protein, wherein the non-hybridizable portion has been modified to create the protein recognition site, wherein the modification is effected by connecting to said non-hybridizable portion a moiety selected from the group consisting of furocoumarin, phenanthridinium and a platinum-containing ligand.

2. A detection probe according to claim 1, wherein the hybridizable portion is covalently associated with one of the strands of the non-hybridizable portion.

3. A detection probe according to claim 1, wherein the hybridizable portion is complementary to the genomic sequence responsible for sickle cell anemia.

4. A detection probe according to claim 1, wherein the modifier is a furocoumarin carrying a protein binding site.

5. A detection probe according to claim 1, including a protein bound to the protein-specific site of the non-hybridizable portion.

6. A detection probe according to claim 5, wherein the protein carries a label.

7. A detection probe according to claim 5, wherein the protein is an antibody specific for a modified double stranded portion.

8. A detection probe according to claim 5, including a labeled protein bound to an immunoglobulin.

9. A detection probe according to claim 5, wherein the nucleic acid is antigenic and is bound through an immunoglobulin to a labeled protein.

10. A process for conducting an assay for the presence of a particular nucleic acid sequence comprising immobilizing either (a) a separation probe or (b) an unknown sample to be assayed on a solid support, subjecting the support to hybridizing conditions in the presence of a detection probe according to claim 1, binding to the non-hybridizable portion of the probe a protein specific thereto, labeling the protein at any stage in the process, and assaying the label.

11. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 1, and assaying the label.

12. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 1, reacting the modified non-hybridizable portion with an antibody specific therefor, and assaying the antibody.

13. A detection probe comprising a hybridizable single stranded portion of nucleic acid connected with a non-hybridizable single stranded nucleic acid portion, the non-hybridizable portion carrying a fluorophore.

14. A detection probe according to claim 13, wherein the fluorophore is coupled to the nucleic acid of the non-hybridizable portion by a furocoumarin.

15. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 14, the furocoumarin carrying a hapten or ligand, and assaying the hapten or ligand.

16. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 14, the furocoumarin carrying a fluorophore, and assaying the fluorophore.

17. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 13, and assaying the fluorophore.

18. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 1, binding to the non-hybridizable portion of the probe a protein specific thereto, labeling the protein at any stage in the process, separating the support from the balance of the material, dissociating the bound protein from the hybridized detection probe, and assaying the dissociated protein.

19. A test kit for assaying for the presence of a particular nucleic acid sequence comprising in one or more containers a detection probe according to claim 1, and a protein recognizable by the protein recognition site of the non-hybridizable portion.

20. A test kit for assaying for the presence of a particular nucleic acid sequence in a sample comprising in one or more containers a detection probe according to claim 1, a separation probe comprising a single stranded nucleic acid immobilized on a support, the single stranded nucleic acid and the hybridizable portion of the detection probe being hybridizable with the sample, and a protein recognizable by the protein recognition site of the non-hybridizable portion of the detection probe.

21. A detection probe comprising a hybridizable single stranded portion of nucleic acid connected to a non-hybridizable, double stranded nucleic acid portion, the non-hybridizable portion including a recognition site for a particular protein, wherein the non-hybridizable portion has been modified to create the protein recognition site, wherein the modification is effected by connecting to said non-hybridizable portion a moiety selected from the group consisting of furocoumarin, phenanthridinium and a platinum-containing ligand.

22. A detection probe according to claim 21, wherein the hybridizable portion is covalently associated with one of the strands of the non-hybridizable portion.

23. A detection probe according to claim 21, wherein the hybridizable portion is complementary to the genomic sequence responsible for sickle cell anemia.

24. A detection probe according to claim 21, wherein the modifier is a furocoumarin carrying a protein binding site.

25. A detection probe according to claim 21, including a protein bound to the protein-specific site of the non-hybridizable portion.

26. A detection probe according to claim 23, wherein the protein carries a label.

27. A detection probe according to claim 23, wherein the protein is an antibody specific for a modified double stranded portion.

28. A detection probe according to claim 23, wherein the protein is an immunoglobulin.

29. A detection probe according to claim 28, including a labeled protein bound to the immunoglobulin.

30. A detection probe according to claim 23, wherein the nucleic acid is antigenic and is bound through an immunoglobulin to a labeled protein.

31. A process for conducting an assay for the presence of a particular nucleic acid sequence comprising immobilizing either (a) a separation probe or (b) an unknown sample to be assayed on a solid support, subjecting the support to hybridizing conditions in the presence of a detection probe according to claim 21, binding to the non-hybridizable portion of the probe a protein specific thereto, labeling the protein at any stage in the process, and assaying the label.

32. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 21, and assaying the label.

33. A process for conducting an assay for the presence of a particular nucleic acid sequence comprising immobilizing either (a) a separation probe or (b) an unknown sample to be assayed on a solid support, subjecting the support to hybridization in the presence of a detection probe according to claim 21, reacting the modified non-hybridizable portion with an antibody specific therefor, and assaying the antibody.

34. A detectionn probe comprising a hybridizable single stranded portion of nucleic acid connected with a non-hybridizable double stranded nucleic acid portion, the non-hybridizable portion carrying a fluorophore.

35. A detection probe according to claim 34, wherein the fluorophore is coupled to the nucleic acid of the non-hybridizable portion by a furocoumarin.

36. A process for conducting an assay for the presence of a particular nucleic acid sequence comprising immobilizing either (a) a separation probe or (b) an unknown sample to be assayed on a solid support, subjecting the support to hybridizing conditions in the presence of a detection probe according to claim 24, the furocoumarin carrying a hapten or ligand, and assaying the hapten or ligand.

37. A process for conducting an assay for the presence of a particular nucleic acid sequence comprising immobilizing either (a) a separation probe or (b) an unknown sample to be assayed on a solid support, subjecting the support to hybridizing conditions in the presence of a detection probe according to claim 34, the furocoumarin carrying a fluorophore, and assaying the fluorophore.

38. A process for conducting an assay for the presence of a particular nucleic acid sequence comprising immobilizing either (a) a separation probe or (b) an unknown sample to be assayed on a solid support, subjecting the support to hybridizing conditions in the presence of a detection probe according to claim 34, and assaying the fluorophore.

39. A process for conducting an assay for the presence of a particular nucleic acid sequence comprising immobilizing either (a) a separation probe or (b) an unknown sample to be assayed on a solid support, subjecting the support to hybridizing conditions in the presence of a detection probe according to claim 21, binding to the non-hybridizable portion of the probe a protein specific thereto, labeling the protein at any stage in the process, separating the support from the balance of the material, dissociating the bound protein from the hybridized detection probe, and assaying the dissociated protein.

40. A test kit for assaying for the presence of a particular nucleic acid sequence comprising in one or more containers a detection probe according to claim 21, and a protein recognizable by the protein recognition site of the non-hybridizable portion.

41. A test kit for assaying for the presence of a particular nucleic acid sequence in a sample comprising in one or more containers a detection probe according to claim 21, a separation probe comprising a single stranded nucleic acid immobilized on a support, the single stranded nucleic acid and the hybridizable portion of the detection probe being hybridizable with the sample, and a protein recognizable by the protein recognition site of the non-hybridizable portion of the detection probe.

42. A method for determining whether the DNA contained in a test sample includes a particular nucleic acid sequence, comprising the steps of:
 (a) extracting nucleic acids from the test sample,
 (b) digesting the extracted nucleic acids with a restriction enzyme thereby to cleave the DNA or not at a particular sequence, depending on whether or not a restriction enzyme recognition site is present in the sequence,
 (c) treating the product of step (b) to form single-stranded nucleic acids,
 (d) contacting the single-stranded nucleic acids produced in step (c) with a first and a second polynucleotide probe, each of said probes being complementary to respective first and second portions of said sequence to be detected, said first probe being in solution with said test sample, said first probe being a probe according to claim 1, said second probe being attached to a solid support, the two portions being non-overlapping and immediately adjacent to the restriction site in question, the restriction site being between the first and second portions, such contact being performed under conditions favorable to hybridization of said first and second probes to said sequence to be detected, hybridizationn with both of said probes being dependent upon whether in step (b) restriction did not occur, said first probe being incorporated with distinguishable label,
 (e) separating, by means of said second probe, (i) any resulting dual hybridization product comprising said sequence to be detected hybridized to both said labeled first probe and said second probe, from (ii) any unhybridized and singly hybridized labeled first probe, and (f) detecting by means of said label any of said separated dual hybridization product which may be present.

43. A method for determining whether the DNA contained in a test sample includes a particular nucleic acid sequence, comprising the steps of:
(a) extracting nucleic acids from the test sample,
(b) digesting the extracted nucleic acids with a restriction enzyme thereby to cleave the DNA or not at a particular sequence, depending on whether or not a restriction enzyme recognition site is present in the sequence,
(c) treating the product of step (b) to form single-stranded nucleic acids,
(d) contacting the single stranded nucleic acids produced in step (c) with a first and a second polynucleotide probe, each of said probes being complementary to respective first and second portions of said sequence to be detected, said first probe being in solution with said test sample, said first probe being a probe according to claim 27, said second probe being attached to a solid support, the two portions being non-overlapping and immediately adjacent to the restriction site in question, the restriction site being between the first and second portions, such contact being performed under conditions favorable to hybridization of said first and second probes to said sequence to be detected, hybridization with both of said probes being dependent upon whether in step (b) restriction did not occur, said first probe being incorporated with a distinguishable label,
(e) separating, by means of said second probe, (i) any resulting dual hybridization product comprising said sequence to be detected hybridized to both said labeled first probe and said second probe, from (ii) any unhybridized and singly hybridized labeled first probe, and
(f) detecting by means of said label any of said separated dual hybridization product which may be present.

44. A detection probe according to claim 4, wherein the protein binding site comprises biotin.

45. A detection probe according to claim 24, wherein the protein binding site comprises biotin.

46. A detection probe comprising a hybridizable single stranded portion of nucleic acid connected to a non-hybridizable, single straded nucleic acid portion, the non-hybridizable portion modified by a fluorescent moiety.

47. A detection probe according to claim 46, wherein the fluorescent moiety is linked to a furocourmarin.

48. A detection probe according to claim 46, wherein the fluorescent moiety comprises fluorescein.

49. A detection probe comprising a hybridizable double stranded portion of nucleic acid connected to a non-hybridizable, double stranded nucleic acid portion, the non-hybridizable portion modified by a fluoroescent moiety.

50. A detection probe according to claim 49, wherein the fluorescent moiety is linked to a furocourmarin.

51. A detection probe according to claim 49, wherein the fluorescent moiety comprises fluorescein.

* * * * *

UNITED STATES PATENT AND TRADEMARK OFFICE
CERTIFICATE OF CORRECTION

PATENT NO. : 4,724,202
DATED : Feb. 9, 1988
INVENTOR(S) : Dattagupta et al.

It is certified that error appears in the above-identified patent and that said Letters Patent is hereby corrected as shown below:

Col. 9, line 1      Delete "HCl" and substitute --KCl--
Col. 16, line 9     Delete "14" and substitute --4--
Col. 17, line 43    Correct spelling of --detection--
Col. 18, line 61    Insert --a-- after "with"
Col. 19, line 21    Delete "27" and substitute --21--

Signed and Sealed this

Thirtieth Day of August, 1988

Attest:

DONALD J. QUIGG

*Attesting Officer*        *Commissioner of Patents and Trademarks*